(12) United States Patent
Ferrani-Kile

(10) Patent No.: US 8,470,745 B2
(45) Date of Patent: Jun. 25, 2013

(54) METHODS AND COMPOSITIONS FOR OBTAINING AND USING BIOLOGICALLY ACTIVE MULTI-PROTEIN COMPLEXES

(76) Inventor: Karima Ferrani-Kile, Austin, TX (US)

( * ) Notice: Subject to any disclaimer, the term of this patent is extended or adjusted under 35 U.S.C. 154(b) by 0 days.

(21) Appl. No.: 13/370,962

(22) Filed: Feb. 10, 2012

(65) Prior Publication Data

US 2012/0157345 A1 Jun. 21, 2012

Related U.S. Application Data

(63) Continuation of application No. 12/295,112, filed as application No. PCT/US2007/065611 on Mar. 30, 2007, now abandoned.

(60) Provisional application No. 60/787,686, filed on Mar. 31, 2006.

(51) Int. Cl.
*C40B 30/04* (2006.01)
*C07K 17/00* (2006.01)

(52) U.S. Cl.
USPC ........................ 506/9; 506/7; 435/21; 435/7.1

(58) Field of Classification Search
USPC ...................................... 506/9, 7; 435/7.1, 21
See application file for complete search history.

(56) References Cited

U.S. PATENT DOCUMENTS

| 6,936,457 B1 | 8/2005 | Gillespie et al. |
| 7,358,057 B2 | 4/2008 | Wang et al. |
| 2002/0146765 A1 | 10/2002 | Adamczewski et al. |
| 2005/0170360 A1 | 8/2005 | Papke et al. |
| 2006/0057614 A1 | 3/2006 | Heintz |
| 2006/0142188 A1 | 6/2006 | Wang et al. |

OTHER PUBLICATIONS

Fitzgerald et al., Multiprotein expression strategy for strucutal biology of eukaryotic complexes, Structure, Sep. 2007, vol. 15, No. 3, pp. 275-279.
Bertone et al., Advances in functional protein microarray technology, FEBS Journal, Nov. 2005, vol. 272, No. 21, pp. 5400-5411.

*Primary Examiner* — T. D. Wessendorf
(74) *Attorney, Agent, or Firm* — Whitham, Curtis, Christofferson & Cook, P.C.

(57) ABSTRACT

Methods for isolating and using multi-protein complexes that are biologically active are provided. The complexes contain one or more proteins of interest (e.g. a receptor, ion channel, etc.) and associates scaffolding proteins such as phosphatases, kinases and post synaptic density components. Buffers that do not contain denaturing agents and which may be used to isolate the multi-protein complexes are also provided, as are protein arrays containing the biologically active multi-protein complexes. The protein arrays may be used, for example, for high throughput screening assays.

5 Claims, 7 Drawing Sheets

Receptor in the cell

ID: 8,470,745 B2

METHODS AND COMPOSITIONS FOR OBTAINING AND USING BIOLOGICALLY ACTIVE MULTI-PROTEIN COMPLEXES

This application is a CON of Ser. No. 12/295,112 Apr. 20, 2009 ABN which is a 371 of PCT/US2007/065611 Mar. 30, 2007 which claims benefit of 60/787,686 Mar. 31, 2006.

BACKGROUND OF THE INVENTION

1. Field of the Invention

The invention generally relates to methods for isolating and using multi-protein complexes that are biologically active. In particular, the invention provides buffers that may be used to isolate the multi-protein complexes in a biologically active form, and protein arrays that contain biologically active multi-protein complexes that are isolated using such buffers, as well as methods for their use in high throughput screening assays.

2. Background of the Invention

Biotechnology companies are increasingly relying on screening methods and technologies to identify lead compounds with therapeutic capabilities. Such methods typically involve the use of immobilized biologically relevant molecules such as nucleic acids and proteins. The technology for manipulating nucleic acids is well developed due in part to the relative simplicity of DNA and RNA molecules and the hybridization reactions they undergo. In contrast, the development of protein arrays is much more challenging due to the complexity of protein-ligand interactions.

Several factors contribute to this complexity. The 20 (common) amino acids that make up proteins are each unique and possess widely differing chemical properties. Thus, individual proteins, each with their own characteristic amino acid composition, also differ widely from one another, and exhibit widely differing biological activities. Further, in addition to linear primary structure, native "folded" proteins possess characteristic secondary (and sometimes tertiary and quaternary) 3-dimensional structural elements that are necessary for proper functioning. Maintenance of this native structure depends in part on the surrounding environment (e.g. pH, temperature, hydrophilicity/hydrophobicity of medium, etc.). In addition, in order to carry out its characteristic activity, a protein often must be in contact with and interact with other biological molecules. For example, many proteins require the presence of various cofactors, activators, and/or other proteins (e.g. scaffolding proteins) in order to be active. In vitro reproduction of the in vivo-like conditions necessary for proper protein functioning can thus be extremely challenging.

Nevertheless, a large number of protein array-based products for a range of applications have been introduced. Progress has been made in developing so-called interaction protein arrays in which a number of proteins (or polypeptides or peptides) are immobilized on a surface and specific interactions with soluble proteins (e.g. in a biological test sample) are detected. Such interactions between immobilized proteins and soluble proteins are intended to mimic biochemical events that take place in a cell or biological fluid in vivo. However, the physiological relevance of data obtained with such biochips is questionable. In a cellular environment, a biochemical reaction will take place only if the reactants are suitably juxtaposed (e.g. in a sub-cellular compartment, on the surface of a cell, etc). Bio-molecules that come together on the surface of a biochip may or may not actually be co-localized in vivo, and, conversely, bio-molecules that come together in vivo may or may not associate properly on the surface of a biochip.

This challenge is particularly acute when dealing with large, multi-protein complexes such as those involved in cell signaling. The assembly of receptors and signal transduction proteins into large multi-protein complexes has emerged as a general mechanism of cellular signaling (see review, Pawson and Scott, 1997), and processes such as phosphorylation, glycosylation, and protein-protein interaction are considered to be major regulators of receptor function. Due to their importance in many cellular processes, methods for isolating and using such complexes are in high demand. Unfortunately, buffers that are routinely used for immunoprecipitation of such protein complexes typically contain sodium sodecyl sulfate (SDS), sodium deoxycholate and/or other detergents which can alter the activity of the receptor itself, or the activity of proteins that surround and interact with the receptor in vivo, such as kinases and phosphatases The prior art has thus-far failed to provide methods for reliably isolating multi-protein complexes in a biologically active form. The prior art has also thus-far failed to provide arrays of immobilized, biologically active multi-protein complexes in which the in vivo associations between the proteins in the complex are maintained.

SUMMARY OF THE INVENTION

The present invention provides methods for the extraction, isolation and use of functional, biologically active multi-protein complexes. Such multi-protein complexes include both at least one principle protein of interest (e.g. an ion channel, a receptor, etc.) together with their scaffolding or support proteins (e.g. phosphatases, kinases, post-synaptic density components, anchoring, chaperone and adaptor proteins, etc.). As illustrated herein, the biologically active multi-protein complexes isolated according to the methods of the invention can be successfully immobilized in vitro and used for diagnostic and testing purposes. Importantly, the biochemical events that occur in the isolated, immobilized multi-protein complexes were shown to closely emulate those that occur in brain slices and heart tissue. Such immobilized complexes may be used to build protein and high throughput screening (HTS) arrays, a kit, as well as other tools for research and drug discovery.

It is an object of this invention to provide an isolated multiprotein complex in vitro in a form which retains its biological activity. The complex comprises one or more proteins of interest and one or more scaffolding proteins. In one embodiment, the protein of interest is multimeric, and the protein of interest may be, for example, a receptor or ion channel. The scaffolding proteins may be, for example, phosphatases, kinases, and post synaptic density components. In one embodiment, the protein of interest is N-methyl-D-aspartate receptor. In another embodiment, the protein of interest is gamma-amino butyric acid receptor. In another embodiment, the protein of interest is $\alpha$-7 nicotinic acetylcholine receptor. In yet another embodiment, the protein of interest is cyclic nucleotide-gated ion channel—HCN4.

The invention also provides an array comprising a substrate; and one or more isolated multiprotein complexes associated with the substrate. The one or more isolated multiprotein complexes comprise one or more proteins of interest and one or more scaffolding proteins, and the one or more isolated multiprotein complexes are biologically active. In one embodiment of the invention, one or more isolated multiprotein complexes are immobilized on the substrate via an antibody that is attached to the substrate, the antibody being specific for (or binding selectively to) a component of the complex, e.g. to a subunit of a protein of interest. In one embodiment, the protein of interest is multimeric, and the protein of interest may be, for example, a receptor or ion channel. The scaffolding proteins may be, for example, phosphatases, kinases, and post synaptic density components. In one embodiment, the protein of interest is N-methyl-D-aspartate receptor. In another embodiment, the protein of interest is gamma-amino butyric acid receptor. In another embodiment, the protein of interest is α-7 nicotinic acetylcholine receptor. In yet another embodiment, the protein of interest is cyclic nucleotide-gated ion channel—HCN4. In one embodiment, the array is a multiwell plate. In yet another embodiment, the isolated multiprotein complexes are associated with the substrate in a manner suitable for high throughput screening.

The invention further provides a method of assaying for biological activity or chemical reactivity. The method comprises the steps of: 1) providing an isolated multiprotein complex in vitro in a form which retains biological activity, the multiprotein complex comprising one or more proteins of interest and one or more scaffolding proteins; 2) exposing the isolated multiprotein complex to one or more substances; and 3) detecting a presence or absence of a biological activity or chemical reactivity of the multiprotein complex to the one or more substances. In one embodiment, the providing step is performed with the isolated multiprotein complex in a liquid solution or suspension. In another embodiment, the providing step is performed with the isolated multiprotein complex associated with a substrate. The isolated multiprotein complex may be associated with the substrate in a manner that is suitable for high throughput screening. The detecting step detects changes in at least one of the following: chemiluminescence, surface plasmon resonance, phosphorescence, fluorescence, and UV/Vis properties. In one embodiment, the biological activity is a change in phosphorylation. In another embodiment, the biological activity is a change in protein-protein interaction.

The invention further provides a method of preparing an assay for biological activity or chemical reactivity. The method comprises the step of isolating a multiprotein complex from a biological sample so that the multiprotein complex is present in vitro in a form which retains its biological activity. The multiprotein complex comprises one or more proteins of interest and one or more scaffolding proteins. In one embodiment of the invention, the step of isolating employs a composition which comprises one or more non-denaturing detergents, one or more reducing agents, one or more buffering agents, one or more chelating agents, and one or more protease inhibitors. In one embodiment, the composition comprises 0.1% Triton X-100, 0.2% β-mercaptoethanol, 50 mM Tris-HCl, 5 mM EDTA, 5 mM EGTA, and 1 mM phenylmethylsulfonyl fluoride, and has a pH of approximately 7.5.

The invention further provides a kit comprising, 1) an isolated multiprotein complex in vitro in a form which retains its biological activity, the isolated multiprotein complex comprising one or more proteins of interest and one or more scaffolding proteins, wherein the isolated multiprotein complex is present in a non-denaturing buffer; 2) reaction buffer; 3) blocking buffer; and 4) instructions for use. The isolated multiprotein complex may be immobilized on a substrate, or may be in solution. In one embodiment, the kit further comprises antibodies for the detection of phosphorylated residues of the receptor subunit, for the receptor subunits themselves, and/or for other proteins in the complexes. The antibodies may be conjugated to a detectable label such as a fluorescent dye. Alternatively, a detectable label that the end-user of the kit conjugates to the antibodies may be provided.

DETAILED DESCRIPTION OF THE PREFERRED EMBODIMENTS OF THE INVENTION

Figure 1A:
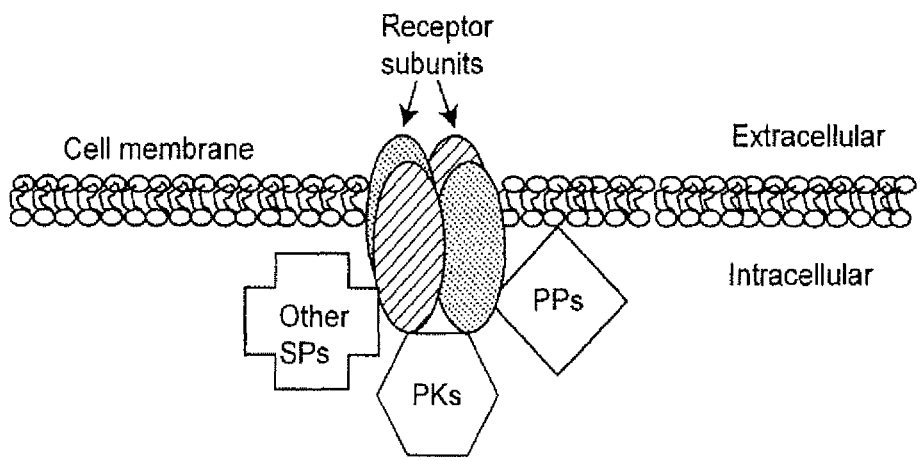
FIG. 1A-D. Schematic representation of the isolation method of the invention using an ion channel receptor complex as an example. A, the intact multiprotein complex in the cellular membrane; B, solubilization of the protein complex in a specially formulated buffer of the invention; C, bottom panel: receptor complex solubilized in immunoprecipitation buffer; top panel: substrate with anti-subunit antibody attached to the surface; D, substrate with intact multiprotein complex immobilized via the antibody. PP=protein phosphatases; PK=protein kinases; SP=scaffolding proteins; RS=receptor subunit.

The present invention provides methods for the extraction and isolation of functional, biologically active multi-protein complexes, and methods of using them in vitro. During such in vitro use, the complexes retain their biological activity, because they are isolated and maintained under conditions that preserve their native, in vivo association with scaffolding proteins. Thus, the form of protein complexes isolated in this manner closely resembles that of the protein complex in vivo. Such multi-protein complexes typically include at least one principle or chief protein of interest together with one or more scaffolding or support proteins that are associated with the protein of interest in vivo. The protein of interest may be comprised of a single or multiple subunits (and multiple subunits may be the same or different), and may have associated with it one or more scaffolding proteins, which may also be the same or different. As described in more detail below, protein arrays may be prepared by immobilizing the complexes, and such arrays may be used for a variety of purposes, e.g. for HTS, diagnostics, research, etc.

In the past, buffers used for solubilization/immunoprecipitation of proteins, particularly for proteins associated with membranes, typically contained SDS, sodium deoxycholate or other detergents, and also inhibitors of kinases and phophatases. Such detergents can denature and/or alter the activity of the protein of interest and the so-called scaffolding proteins that surround the protein of interest (e.g. kinases, phosphatases, structural support proteins, post synaptic density components etc.). In contrast, the solubilization/immunoprecipitation buffers used in the methods of the present invention are specifically formulated to solubilize the protein of interest and its associated scaffolding proteins without disassociating, denaturing and/or inactivating them. The result is that intact, multi-protein complexes that retain their in vivo characteristics are obtained. Such complexes display physiologically relevant properties such as activation, inactivation, phosphorylation/dephosphorylation, glycosylation/deglycosylation, protein-protein interaction, ligand binding, interactions within the complex, etc. In general, the protein(s) of interest are full-length proteins.

For the novel solubilization/immunoprecipitation buffers of the invention, key features are 1) the buffers do not contain denaturing agents i.e. they are substantially non-denaturing buffers; and, 2) they contain agents that prevent kinase and phosphatase inhibition so that kinases and phosphatases that are components of the complex retain their activity. The term "substantially non-denaturing" means that the buffers do not cause substantial irreversible loss of functional activity of the protein nor of the enzymes present in the complex. In other words, solubilization of the proteins in the buffer does not cause irreversible loss of greater than about 75%, or preferably greater than about 50%, or more preferably greater than about 40, 30, 20, 10, or even 5% of the functional activity. Most preferably, exposure of the proteins to the buffer does not cause any decrease in functional activity.

A general composition for a substantially non-denaturing solubilization/immunoprecipitation buffer is as follows:

1. One or more non-denaturing detergents in a total (combined) weight/volume percentage of from about 0.001% to about 10%, and preferably from about 0.5% to about 5%, and most preferably from about 0.1% to about 1%, with about 0.1% being a preferable concentration.

Representative non-denaturing detergents that may be used in the buffer include but are not limited to various nonionic detergents/surfactants such as Triton X-100 and other Pluronic detergents (tri-block copolymers of ethylene oxide and propylene oxide); TritonX-114 (Triton-X family), Triton-N, Triton-CF, Lubrol WX, Brij35, Brij96 and Brij98 (Brij family), Cholate, 3-[(3-cholamidopropyl)dimethylammonio] propane sulfonic acid (CHAPS), 3-[(3-cholamidopropyl) dimethylammonio]-2-hydroxy-1-propanesulfonate (CHAPSO), n-Dodecyl-β-D-Maltoside, Octyl β-Glucoside, Octyl β-Thioglucopyranoside, Nonidet® P 40, Tween, n-Dodecyl a-D-maltoside, Tyloxapol, Triethylene glycol monooctyl ether and family, Tetraethylenepentamine pentahydrochloride and family, Tergitol®, sucrose, sucrose monolaurate, sucrose monodecanoate, Span®, Saponin, Pril®, Cremophor®, N-Octanoyl-N-methylglucamine and family, Igepal® Ethylene glycol monooctyl ether and family, Digitonin, and detergents referenced at the web site located at abrf.org/ABRFNews/1997/December1997/dec97detergent, etc.

2. One or more reducing agents in a total weight/volume percentage of from about 0.05 to 5%, preferably from about 0.5 to about 2.5%, and most preferably about 1%.

Representative reducing agents that may be used in the buffer include but are not limited to β-mercaptoethanol, dithiothreitol (DTT) Tris(2-Carboxyethyl)-Phosphine (TCEP), L-cysteine, glutathione, etc.

3. One or more buffering agents that maintain the pH in the range of from about 6.5 to about 8.5, preferably from about 7 to about 8, and most preferably from about 7.5. The total (combined) concentration of the buffering agents will generally be in the range of about 1 to 500 mM, preferably from about 5 to about 100 mM, and more preferably from about 10 to about 75 mM, with about 10, 20 30, 40 and 50 mM being the most preferable concentrations.

Representative buffering agents that may be used in the buffer include but are not limited to Tris (Tris(hydroxymethyl)aminomethane); PIPES (piperazine-1,4-bis(2-ethanesulphonic acid)); HEPES (N-(2-Hydroxyethyl)piperazine-N'-(2-ethanesulfonic acid); various phosphate containing buffers; RIPA (RadioImmunoPrecipitation Assay), TBS (Tris Buffered Saline), PBS (Phosphate Buffered Saline), MES (4-Morpholineethanesulfonic acid) 2-(N-morpholino) propane sulfonic acid (MOPS), N-cyclohexyl-3-aminopropanesulfonic acid (CAPS), N-cyclohexyl-2-hydroxyl3-aminopropanesulfonic acid (CAPSO), 2-(N-cyclohexylamino)ethane sulfonic acid (CHES), various sugars e.g. sucrose may be used to facilitate keeping the complex intact; and the like.

4. One or more chelating agents, each being present at a concentration of from about 0.1 to 50 mM, preferably from about 1 to about 10 mM, and most preferably about 5 mM.

Representative chelating agents that may be used in the buffer include but are not limited to EDTA (Ethylenediaminetetraacetic acid Disodium salt), EGTA (Ethyleneglycol-O,O'-bis(2-aminoethyl)-N,N,N',N'-tetraacetic acid), HEDTA (N-(2-Hydroxyethyl)ethylenediamine-N,N',N'-triacetic acid Trisodium salt), NTA (Nitrilotriacetic acid), 2,2'-Bipyridyl, Dimercaptopropanol, Salicylic acid, TEA (Triethanolamine), etc.

5. Protease inhibitors, e.g. a "cocktail" of protease inhibitors present in an amount ranging from about 0.1 to about 100 mg/ml, preferably from about 1 to about 50 mg/ml, more preferably about 5 to about 25 mg/ml, and most preferably about 10 mg/ml.

Optionally, specific protease inhibitors such as phenylmethylsulfonyl fluoride (PMSF) may also be a component, generally in a concentration of from about 0.1 to 10 mM, preferably from about 0.5 to about 5 mM, and most preferably at about 1 mM.

Representative protease inhibitors that may be used in the buffer include but are not limited to "cocktails" of protease inhibitors such as those that are commercially available (e.g. Protease inhibitor cocktail from BD Biosciences Pharmingen, BioVision, Calbiochem (set I to VIII), ProteCEASE™ from G Biosciences, etc.). In addition, individual protease inhibitors may also be included, examples of which include but are not limited to pheynymethylsulfonyl flouride (PMSF), Amastatin, E-64, Antipain, Elastatinal, Leupeptin, Bestatin, Pepstatin, Benzamidine, 1,10-Phenanthroline, Chymostatin, Phosphoramidon, 3,4-dichloroisocoumarin, TLCK (N-alpha-tosyl-L-lysyl-chloromethyl ketone), DFP (diisopropylfluorophosphate), TPCK (N-tosyl-L-phenylalanyl-chloromethyl ketone), etc.

The composition of one exemplary non-denaturing solubilization/immunoprecipitation buffer is as follows:
0.1% Triton X-100
0.2% β-mercaptoethanol,
50 mM Tris-HCl pH 7.5,
5 mM EDTA,
5 mM EGTA
10 mg/ml of protease inhibitor cocktail
1 mM phenylmethylsulfonyl fluoride (protease inhibitor)

A wide variety of proteins may be isolated using the buffers of the invention. By "isolated" we mean that they have been removed, via human intervention, from an in vivo location or environment i.e. they have been removed from a biological source, and have been manipulated using laboratory techniques to an in vitro form that may be used in the procedures described herein. In some cases, the biological source/environment will be the native mileau e.g. the location in which the protein complex naturally occurs (e.g. tissues, serum, blood, urine, eggs, etc. of an organism). For multiprotein complexes that have been cloned or genetically engineered, the source may be a recombinant organism or cell that produces the complex. In yet other cases, the source of the protein complexes may be cultured cells, which may or may not be genetically engineered. Regardless of the exact biological source or environment of origin, the biologically active multiprotein complexes are separated, removed or taken from the source, and manipulated and used as described herein. The isolated multiprotein complexes may contain various other substances (e.g. salts, ions, buffer components, extraneous cellular material, etc.) without compromising the activity of complexes or their intended use.

Such proteins may be comprised of either of a single subunit (monomers, monomeric) or of multiple subunits (multimers, multimeric). The invention is particularly useful for the isolation of multimeric proteins, and even more particularly for multimeric proteins that reside in biological membranes, and most particularly for multimeric proteins that rely on scaffolding proteins in order to carry out their biological activity. Examples of proteins categories that may be isolated by the methods of the invention include but are not limited to transmembrane receptor proteins (e.g. G-protein-coupled receptors such as: Acetylcholine receptors, Adenosine receptors, Adrenergic receptors, GABA B receptors, Angiotensin receptors, Cannabinoid receptors, Cholecystokinin receptors, Dopamine receptors, Glucagon receptors, Metabotropic glutamate receptors, Histamine receptors, Olfactory receptors, Opioid receptors, Rhodopsin (a photoreceptor), Secretin receptors, Serotonin receptors, except Type-3, Somatostatin receptors, Calcium-sensing receptors, Chemokine receptors etc.; Receptor Tyrosine Kinases such as: Erythropoietin receptor, Insulin receptor, Eph receptors, Insulin-like growth factor 1 (IGF-1) Receptors, etc. Guanylyl cyclase receptors such as: GC-A & GC-B, receptors for Atrial-natriuretic peptide (ANP), etc.; Intracellular receptors such as: Steroid hormone receptor, Thyroid hormone receptor, Retinoid receptor, Peroxisome proliferator-activated receptors (PPARs), IP3 receptors etc.; Ion channel proteins such as: Nicotinic acetylcholine receptors, Glycine receptor, GABA-A, GABA-C receptors (GABA=Gamma-amino butyric acid), N-Methyl-D-aspartate receptor (NMDA) receptor, α-amino-3-hydroxy-5-methylisoxazole-4-propionic acid receptor (also known as AMPA receptor, AMPAR, or quisqualate receptor), Kainate receptor, 5-hydroxytryptamine (5-HT3) receptor, etc. Also included are various phospho-proteins, i.e. polypeptides that can be potentially phosphorylated on at least one residue, which can be tyrosine, serine or threonine, or any combination of the three. Phosphorylation can occur constitutively or be induced.

By "scaffolding proteins" we mean various support proteins that are associated with a protein of interest, and that are necessary in order for the protein of interest to carry out its in vivo biological activities. While a protein may be able to carry out its biological activity to some extent without such scaffolding proteins, typically the activity is attenuated and does not accurately reflect the protein's actual physiologically relevant activity. Scaffolding proteins may serve a wide variety of functions and/or support roles for a protein. For example, they may provide structural support, e.g. to sequester the protein at its site of activity, to cause the protein to achieve and/or maintain its 3-dimensional conformation, etc. Alternatively, scaffolding proteins may modulate the biological activity of the protein by catalyzing chemical modifications of the protein, e.g. phosphorylation/dephosphorylation and/or glycosylation/deglycosylation reactions which, depending on the nature of the protein, may either activate or inactivate the protein. Examples of such scaffolding proteins include but are not limited to various phosphatases, kinases, post synaptic density components, chaperon proteins such as chaperonin, anchoring proteins, adaptor proteins, protein modules, docking proteins, etc. Further examples of scaffolding proteins, include but are not limited to Sterile 5 (Step 5) and AKAP79 anchoring proteins, the 14-3-3 family of adaptor proteins, actin, etc. Scaffolding proteins may be directly associated with the protein of interest (or with one or more subunits of the protein of interest) by any of several means, such as covalently or non-covalently (e.g. by hydrogen or ionic bonding). Alternatively, the scaffolding proteins may be associated indirectly via one or more other scaffolding proteins that make direct contact with the protein.

In some embodiments of the invention, protein kinases and protein phosphatases are of particular interest as scaffolding proteins.

A protein kinase is an enzyme that modifies other proteins. The chemical activity of kinases involves removing a phosphate group from ATP and covalently attaching it to one of three amino acids that have a free hydroxyl group. Most kinases act on both serine and threonine, others act on tyrosine, and a number (dual specificity kinases) act on all three.

Serine/threonine-specific protein kinases are a group of enzymes that catalyze the phosphorylation of serine or threonine residues in proteins, with ATP or other nucleotides as phosphate donors. Serine/threonine protein kinases phosphorylate the OH group of serine or threonine (which have similar sidechains). Examples of serine/threonine protein kinases include but are not limited to Akt1/PKBa, activin-like kinase receptor-4 (ALK4), ARK5, apoptosis signal-regulating kinase 1 (ASK1), Aurora, BrSK1, calmodulin, CaM Kinase, casein kinase, cdk, Cot1, death-associated protein kinase (DAPK), doublecortin and CaM kinase-like 2 (DCAMKL2), dystrophia myotonica-protein kinase (DMPK), DAP kinase related apoptosis inducing protein kinases (DRAM), EF-2 kinase, G-protein-coupled receptor kinase (GRK), Homeodomain-interacting protein kinases (HIPK), heat shock protein (HSP), HSP27, IB kinase or IKK, IL-1 receptor-associated Ser/Thr kinase (IRAK), insulin related receptor (IRR), c-Jun N-terminal kinase/stress-activated protein kinase (JNK/SAPK), LIM kinase, LKB1, lymphocyte-oriented kinase (LOK), mitogen activated protein (MAP), linase/Erk, microtubule-affinity regulating kinase (MARK), mitogen-activated protein kinase (MEK), mitogen-activated protein/ERK kinase kinases (MEKK), maternal embryonic leucine zipper kinase (MELK), misshapen/NIKs-related kinase (MINK), MAP kinase kinase (MKK), mixed-lineage kinase (MLK), Mnk2, myotonic dystrophy kinase-related Cdc42-binding kinase (MRCK), mitogen- and stress-activated protein kinase (MSK), muscle-specific serine kinase (MSSK), mammalian Step 20-like protein kinase (MST), NIMA Related Kinase (NEK), nemo-like kinase (NLK), p38/stress-activated protein kinase (SAPK), PAK, PAR, PAS domain containing serine/threonine kinase (PASK), 3-phosphoinositide-dependent kinase (PDK), phosphorylase kinase, Pim, protein kinase (PK) such as PKA, PKC, PKD, PKG, PKR, PKR agarose, active, p38-related/activated protein kinase (PRAK), protein kinase X (PRKX), receptor-interacting serine/threonine kinase (RIPK), Rho-associated kinase (ROK/ROCK), S6 kinase, salt iinducible kinase (SIK), serine arginine protein kinase (SRPK), (TGFβ)-activated kinase (TAK1), Thousand and One Amino Acid Protein Kinase (TAO), TANK-binding kinase 1 (TBK1), testis-specific serine kinase-1 (TSSK1), Wee1, ZIPK, etc.

Tyrosine-specific protein kinases phosphorylate tyrosine amino acid residues, and are used in signal transduction. They act primarily as growth factor receptors and in downstream signaling from growth factors. Examples of tyrosine-specific protein kinases include but are not limited to Abl, anaplastic lymphoma kinase, Alk, active, Arg, Axl, Blk, Bmx, Brk, Csk, Ddr, DYRK, epidermal growth factor (EGF) and EGF receptor, Eph, erbB/HER, Fer, Fes/Fps, fibroblast growth factor (FGF) and FGF receptor, Fgr, Flt, Fms/colony-stimulating factor (CSF)-1 receptor, Fyn, Hck, homeodomain interacting protein kinase (HIPK), insulin-like growth factor (IGF) and IGF receptor, insulin and insulin receptor, Itk, JAK receptor, Kit, (V654A), linker for activator of T cells (LAT), Lck, Lyn, Mer, Met, MuSK, platelet-derived growth factor (PDGF) and PDGF receptor, PTK5, Pyk2, Ret, Ron, Ros, Rse, Src, Syk, Tie/TEK, Trk, vascular endothelial growth factor (VEGF) and VEGF Receptor, KDR, Yes, ZAP-70, etc.

Dual specificity protein kinases phosphorylate tyrosine, serine and threonine amino acid residues, and are generally used in signal transduction. Examples of dual specificity protein kinases include but are not limited to CLK3, DYRK, MEK, etc.

A protein phosphatase is an enzyme that dephosphorylates its substrate; i.e., it hydrolyses phosphoric acid monoesters into a phosphate ion and a molecule with a free hydroxyl group. Phosphatases can be subdivided based upon their substrate specificity. Tyrosine-specific phosphatases include protein tyrosine phosphatase1B (PTP1B), phosphacan, SHP/SHPTP, and striatum enriched phosphatase (STEP). Serine/threonine specific phosphatases include PP1 (a, β, γ1, γ2), PP2A, PP2B (AKA calcineurin), PP2C, PPP, and PPS.

Dual specificity phosphatases have the ability to dephosphorylate both tyrosine and serine/threonine residues. Examples of dual specificity phosphatases include vaccinia H1 related (VHR) phosphatase.

The methods of the invention are generally carried out by identifying a biological source of the protein of interest. The biological source may be any suitable source of the protein, e.g. tissues, cells, blood, serum, microorganisms such as yeast or bacteria, fungi, plants, blue-green algae, etc. In addition, the protein complexes can be those which have been genetically engineered and expressed in cells, yeast etc. The buffers and methods of the invention are employed to extract, isolate, concentrate, immunoprecipitate, and/or "pull down" and purify the protein complex using standard protein isolation techniques known to those of skill in the art. Herein, terms such as "extract", "isolate" and "purify" may be used interchangeably to refer to the steps involved in obtaining a protein complex in a form that is suitable for use in vitro. The techniques employed may include such steps as obtaining tissues, cells, etc. that contain the protein, homogenizing the tissues/cells with a buffer of the invention, and partially purifying the complexes by e.g. centrifugation, filtration, sodium sulphate precipitation, by size exclusion chromatography (i.e. gel filtration or gel permeation chromatography), etc. Alternatively, proteins of interest may be purified (or further purified) by differential binding to ligands, e.g. by exposure to various entities that non-specifically or specifically bind to the protein of interest. Such entities include but are not limited to antibodies (both mono- and polyclonal), substrates, inhibitors, cofactors, metals, various charged groups (e.g. in anion or cation chromatography), etc. Such methods are known to those of skill in the art, and any suitable method or combination of methods may be used in the isolation of the biologically active multiprotein complexes of the invention, so long as the protective buffers of the invention are employed to preserve the biological activity of the complexes. In a preferred embodiment of the invention, the complexes are isolated by immunoprecipitation using antibodies that are specific for some portion of the protein of interest. Antibodies may be either mono- or polyclonal, and may be specific for any portion of the protein. For example, for a multisubunit protein, the antibodies may be directed to any of the subunits, or even to more than one subunit. Further, more than one type of antibody may be utilized, e.g. mixtures of antibodies which are specific for different subunits may be used. Co-immunoprecipitation is a term that used to describe immunoprecipitating a protein of interest together with its scaffolding proteins, e.g. immunoprecipitating a receptor or ion channel protein, together with its kinases and/or phosphatases.

Once extracted and isolated, the biologically active multiprotein complexes may be used in a variety of ways. Generally, the complexes will be employed in diagnostic and screening assays. This technology holds great potential for basic molecular biology and biochemistry research, serum profiling, protein abundance determination, disease biomarker identification, immune and toxicological response profiling, and pharmaceutical target screening. The form of the complex may be any in which the biological activity is retained. For example, the complexes may be utilized in solution, or they may be attached to a substrate. In a preferred embodiment of the invention, the complexes are immobilized on the surface of a substrate by an immunoprecipitation reaction with an antibody that is attached to the substrate surface. In this embodiment, the antibody serves to effect both the purification of the complex and its immobilization.

Figure 1B:
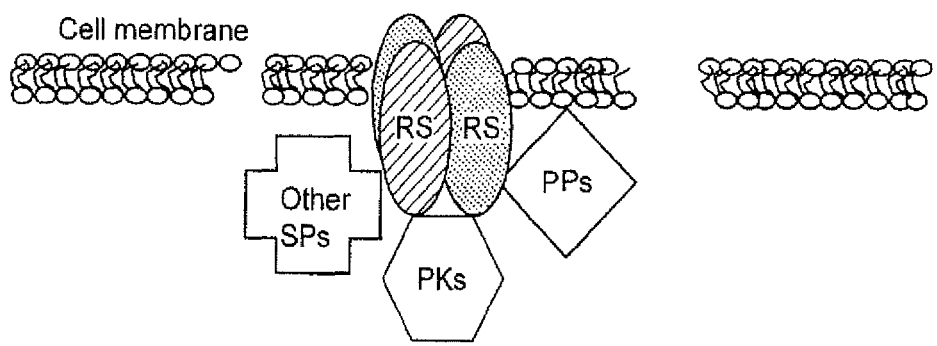
Figure 1C:
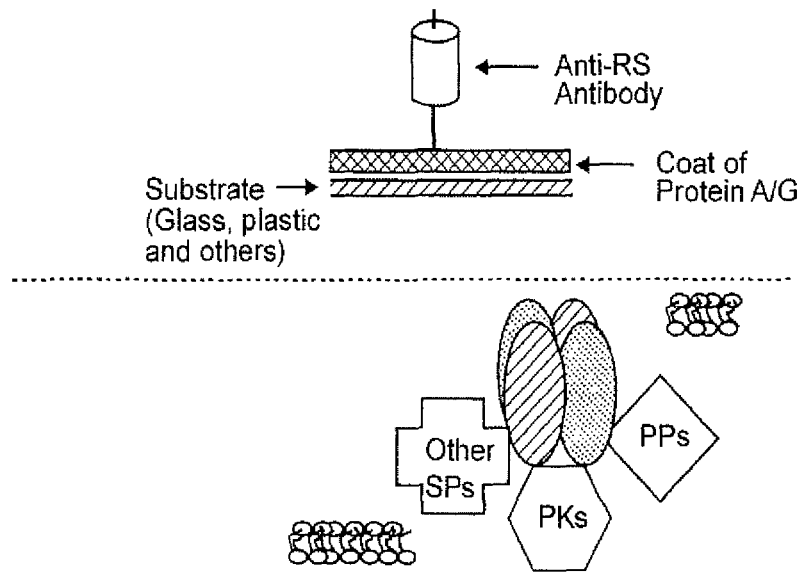
Figure 1D:
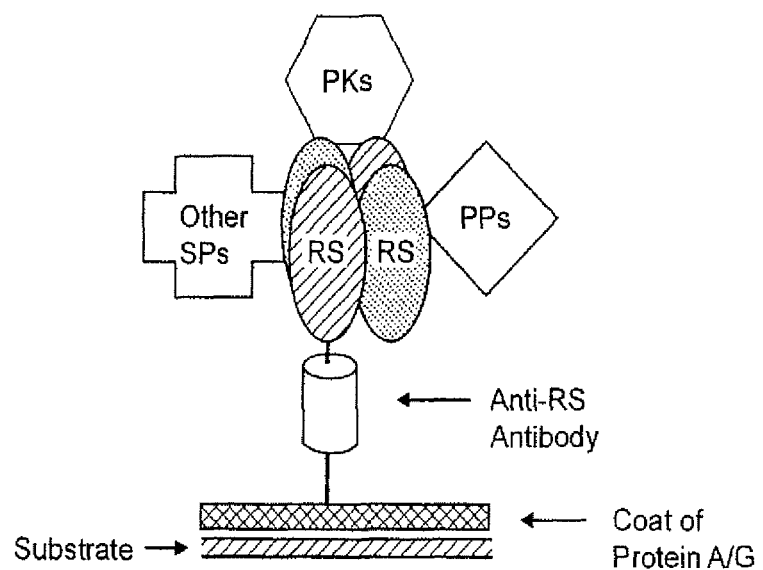
Figure 2A:
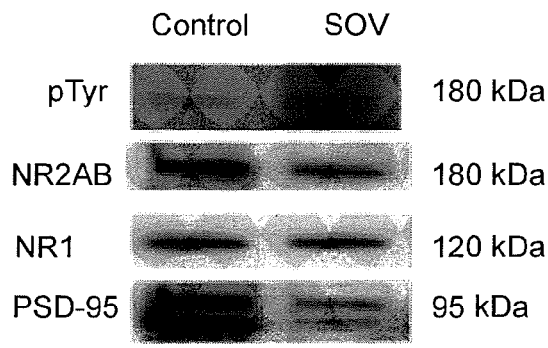
FIG. 2A-D. Immunoblotting detection of isolated NMDAR complexes biological activity: effect of PTP inhibitor SOV on immobilized complexes. A, immunoblots. B-D show quantitation of immunoblot results are expressed as a ratio of pTyr to NR2A/B (B), NR2A/B to NR1 (C) or PSD-95 to NR1 (D). The results are representative of four separate experiments. Data are mean S.E.M. Percent of control (*, $P<0.05$, **, $P<0.01$ control vs SOV).
Figure 2B:
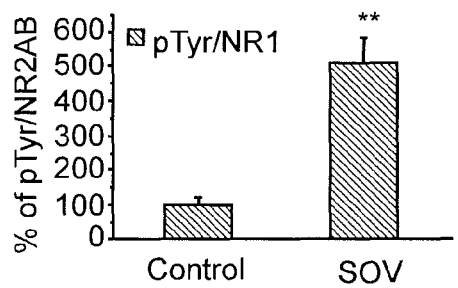
Figure 2C:
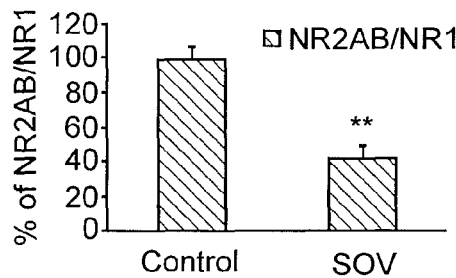
Figure 2D:
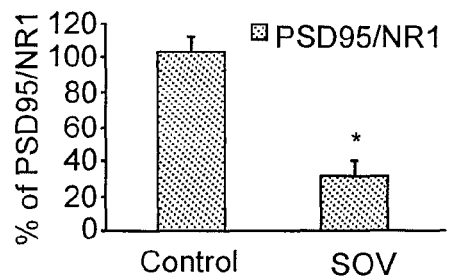

FIG. 1A-D schematically illustrates an embodiment of the invention in which the protein of interest is tetrameric ion channel that is present in a cellular membrane. FIG. 1A shows the ion channel protein embedded in the membrane with associated with phosphatases, protein kinases, and other scaffolding proteins. FIG. 1B shows solubilization of tissues or cells with a buffer of the invention. The bottom panel of FIG. 1C depicts the multiprotein complex in solution; at this stage of purification, other proteins and components of the tissue would be present. The top panel of FIG. 1C shows the surface of a substrate to which is attached an antibody specific for a receptor subunit of the protein of interest. When the solution containing the complex is brought into contact with the immobilized antibody, the antibody captures the complex via the subunit, and the entire multiprotein complex (protein of interest with all subunits plus scaffolding proteins) becomes immobilized on the substrate.

While FIG. 1 illustrates immobilization of the complex on a flat substrate, this need not be the case. The substrate (also referred to as a "solid support" or "carrier") refers to an insoluble matrix, and may (optionally) have a rigid or semi-rigid surface. Such substrates may be in any useful form, e.g. beads, pellets, disks, chips, dishes, multi-well plates, wafers, wires, filaments, tubes, flexible strips, thread-like structures, etc., or any combination of these, and may be of any suitable material, e.g. glass, plastic, various polymers, metals (e.g. gold, platinum, silver, copper, aluminum), silicon, silicon oxide, silicon nitride, tantalum oxide, titanium oxide, indium tin oxide, magnesium oxide, quartz, silica and combinations thereof, etc. Further, the surface may be part of a larger construct, e.g. a flat surface may be the bottom of a well or depression in a multiwell plate such as the 96-, 384- or 1536-well plates that are known in the art. In addition, the immobilization of the complex may be more complex than that which is illustrated, e.g. biotin-streptavadin, secondary antibodies, magnetic features, etc., may form part of the immobilization strategy. Any strategy for immobilizing the multi-protein complex may be utilized so long as the complex is retained on the substrate, and so long as the means of retention does not appreciably interfere with the biological activity of the complex. Immobilization substrates that may be employed in the invention include but are not limited to surfaces of glass, slides, beads, membranes (e.g. polyvinylidene fluoride (PVDF) and nitrocellulose), various polymer surfaces, silicon surfaces, etc.

The isolated multiprotein complexes of the invention, whether immobilized or free in solution, retain or exhibit their characteristic, physiologically relevant biological activity. By "retain their biological activity", we mean that the level of activity exhibited by the protein complex is at least about 50 to 100% (or more) and preferably about 75 to 100% (or more) of that of the multiprotein complex when it is in vivo. For complexes for which the level of in vivo activity is not known, the complexes may be described simply as "biologically active", in that they are capable of carrying out in vitro the biochemical reactions that they perform in vivo, at a level that is detectable by known methods. Alternatively, for proteins for which a standard measure of reactivity has been established in the art, but which has not heretofore been measured in a complex, the multiprotein complexes of the invention will generally exhibit from about 50 to 100%, or preferably 75 to 100%, or even more than 100%, of the previously established standard activity, although in some cases the level of activity of the complex may actually be less. This is because the activity of the multiprotein complexes described herein more closely resembles that of the complexes when they are in their native, in vivo environment. Those of skill in the art are familiar with the development and standardization of measurements of protein activity.

The activity of the multiprotein complexes of the invention, either immobilized or free in solution, may be measured by any of a wide variety of techniques that are known to those of skill in the art. Examples include but are not limited to fluorescence, chemiluminescence, radioactivity, colorimetry, mass spectroscopy, surface plasmon resonance, reporter enzymes, affinity ligands, monoclonal or polyclonal antibodies that selectively bind to different states of the complex (e.g. antibodies that selectively bind to phosphorylated residues, or to residues that are not phosphorylated), radioimmunoassays, immobilized metal affinity chromatography (IMAC), two-dimensional electrophoretic gel separation (2-D PAGE) coupled with mass spectrometry detection, liquid chromatography separation coupled with mass spectrometry detection, etc. U.S. Pat. No. 6,875,618 to Bandara et al., the entire contents of which is incorporated by reference, describes some of these and other methods. In particular, fluorescence detection is the basis of most assays used in drug discovery and high throughput screening today (Lakowicz, 1999; Asian et al., 2005). Recently, advances in fluorescence-based detection techniques and automation technologies have facilitated the miniaturization of assays from 96 wells into a 384 and 1536-well HTS assays. Thus, in a preferred embodiment of the invention, immunofluorescence is used as the detection method. Such techniques may be used, for example, to detect changes in the phosphorylation status of a protein, or conformational changes, or changes that result from ligand binding, etc.

A preferred embodiment of the invention then is a protein array in which the biologically active multiprotein complexes are immobilized on a substrate that is suitable for high throughput screening assays. "High throughput" refers to the ability to process large amounts of samples in a given process, method or assay, etc. In a preferred embodiment, the high throughout process is conducted with an automated machine(s), which is optionally controlled by computer software, or manually, or both. Such arrays may contain a single type of multiprotein complex, e.g. all the complexes comprise a single type of protein of interest such as a particular ion channel. Alternatively, mixed or hybrid arrays are also contemplated in which a plurality of types of complexes are immobilized. Further, other types of molecules may also be included in a mixed array. Any combination of useful molecules may be present on the arrays, so long as the biological activity of the multiprotein complexes is not compromised. Such assays may include hundreds or even thousands of multiprotein complexes.

Such arrays may be used for small or large-scale detection of candidate modulators of the complexes, e.g. modulators of post-translational modifications of receptor complexes. "Post-translational modification" refers to any changes/modification that can be made to a native polypeptide sequence after ist initial translation. Examples include but are not limited to phosphorylation/dephosphorylation, glycosylation/deglycosylation, prenylation, myristoylation, palmitoylation, limited digestion, irreversible conformation change, methylation, acetylation, modification of amino acid side chain or the amino or carboxy terminus, changes in oxidation, disulfide-bond formation, various protein-protein interactions, etc. The effect of the candidate modulator (e.g. an activator or inhibitor) can be detected by measuring, for example, changes in levels of serine, threonine and/or tyrosine phosphorylation and/or of protein-protein interactions between the receptor subunits and/or protein-protein interactions between the receptor subunits and other proteins. This invention can also be used to screen for agents that bind to the subunit or to other proteins of the complex regardless of whether this binding results in a change in receptor activity; such agents can be molecules, peptides, polypeptides, lipids, DNA, RNA, or other ligands, etc. Such assays are useful as drug-discovery tools, and also as research tools to understand the role of each scaffolding protein in the intricate mechanism of receptor complex regulation, and to identify novel targets for receptor regulation within the multi-protein complex. While performing such assays, any suitable buffering system may be used, so long as the components do not attenuate the biological activity of the multiprotein complex.

The complexes may thus be used to screen any of a wide variety of candidate modulators of the biological or chemical activity of the protein of interest, e.g. "small molecules" that are designed to fit into binding sites of the protein, potential activators or inhibitors of the protein (either reversible or irreversible), various specific and non-specific ligands, which may include other proteins; other protein complexes, polypeptides and peptides; nucleic acids; lipids; polysaccharides; chemicals; various natural products; various cofactors; enzyme substrates; and the like. Any compound of interest may be screened using the biologically active multiprotein complexes of the invention. Exemplary activities that may be detected include but are not limited to kinase activity, protease activity, phosphatase activity, glycosidase activity, acetylase activity, chemical group transferring enzymatic activity, changes in conformation and/or folding; various post-translational modifications, etc.

Further, properties of the complexes other than activity may also be of interest and may be measured using various known techniques, e.g. circular dichroism, differential scanning calorimetry, isothermal titration calorimetry, nuclear magnetic resonance, various spectroscopy techniques, etc. In these cases, the complexes are likely to be maintained in solution rather than immobilized.

The invention also provides a kit or kits to carry out the methods described herein. Such kits contain isolated protein complexes in a non-denaturing solubilization/immunoprecipitation buffer. The proteins may be immobilized or free in solution. The kit may also contains other buffers such as reaction and blocking buffers. Monoclonal or polyclonal antibodies that selectively bind the complexes may also be included, e.g. antibodies that selectively bind a protein in the complex when it is phosphorylated, to a protein itself even when it is not phosphorylated. Detectable labels such as fluorescent dyes that can be conjugated to the antibodies, may also be provided in the kit. Alternatively, the antibodies may be provided already conjugated to such detectable labels. Instructions for use of the kit are also included.

The practice of the invention is further illustrated in the ensuing examples.

EXAMPLES

Example 1

Isolation and Immobilization of Biologically Active N-Methyl-D-Aspartate Receptor Protein Complex Abbreviations:
NMDAR, N-Methyl-D-aspartate receptor; PKA, protein kinase A; SOV, sodium orthovanadate; PKC, protein kinase C; PTK, protein tyrosine kinases; PTPs, protein tyrosine phosphates; SFK, src family kinases, PSD-95, postsynaptic density 95; PPs, serine/threonine phosphatases
Materials And Methods:
Antibodies and Chemicals:

For immunoprecipitation, a polyclonal NMDAζ1 antibody (Santa Cruz Biotechnology, Santa Cruz, Calif., USA) was used. For probing the anti-phosphotyrosine (anti-pTyr) 4G10 clone, anti-phosphoNR1 at Ser896 (anti-pSer896), anti-phosphoNRI at Ser897 (anti-pSer897) and anti-PSD-95 (Upstate Biotechnology, Lake Placid, N.Y., USA); anti-NR1 (B.D. Pharmingen, San Diego, Calif., USA), anti-NR2A, anti-NR2B and anti-NR2A/B (recognizing both NR2A and NR2B subunits) antibodies (Chemicon, Temecula, Calif., USA) were used. Alexa dyes and Zenon IgG labeling kits (Molecular Probes, Carlsbad, Calif.) were used for fluorescence studies. Drugs were purchased from Sigma Aldrich, St. Louis, Mo. or from Calbiochem-Novabiochem Corp., San Diego, Calif., USA. Black and colorless pre-coated protein A/G multi-well plates were purchased from Pierce, Rockford, Ill., USA.

Extraction and Immobilization of the Multi Protein Complexes on Pre-Coated 96-Well Plates:

Experiments were performed on cortical tissue obtained from 3 week-old Sprague-Dawley rats. All procedures were conducted in strict adherence with the NIH Guide for the Care and Use of Laboratory Animals. Cortical tissue from 21 day-old rats was solubilized using a syringe in solubilization/immunoprecipitation buffer containing 0.1% Triton X-100, 0.2% β-mercaptoethanol, 50 mM Tris-HCl pH 7.5, 5 mM EDTA, 5 mM EGTA, 10 mg/ml of Sigma protease inhibitor cocktail, 1 mM phenylmethylsulfonyl fluoride. The tissue homogenate was centrifuged (15,000 g for 10 min at 4° C.) to remove insoluble material. The supernatantusprenat was kept at 4° C. and used later for immunoprecipitation. Protein A/G pre-coated 96-well plates (Pierce Biotechnology, Rockford, Ill.) were used for immunoprecipitation of active NMDA receptor complexes. The plates were washed with the solubilization/immunoprecipitation buffer and anti-NR1 antibody (20 μg) was added to each well in 100 μL of extraction buffer. Following a 2 hour incubation at room temperature, the wells were rinsed 3 times with solubilization/immunoprecipitation buffer and 100 μL of supernatant were added to each well. Following 4 hours incubation at 4° C., the wells were washed three times with a reaction buffer containing: 0.2% β-mercaptoethanol, 25 mM Tris-HCl pH 7.5, 30 mM $MgCl_2$, 20 mM $MnCl_2$, 0.5 mM DTT.

Activity Test:

Fifty μL of reaction buffer, 500 μM ATP, and the agents to be tested were added to each well. The control wells contained 50 μL of reaction buffer alone or in the presence 500 μM ATP. All samples were incubated at 30° C. for 1 hour. The reactions were terminated by adding to all the samples a blocking buffer containing [0.5% DOC, 1% NP-40, 0.1% SDS and 150 mM NaCl in 50 mM Tris-Hcl (pH 8.0), 5 mM EDTA, 5 mM EGTA, 10 mg/ml of protease inhibitor cocktail, 1 mM phenylmethylsulfonyl fluoride (protease inhibitor), 5 mM $Na_3VO_4$, 50 mM NaF, 10 mM $NaPP_1$, 25 mM Na-glycerophosphate and 2 μM Microcystin-LR at 4° C. The samples were rinsed three times with the blocking buffer and subjected to Western blotting or immunofluorescence detection.

Fluorescence Detection:

For fluorescence detection experiments, black 96-well plates were used to avoid fluorescence spill over. Following drug treatment, samples in the wells were blocked and rinsed with blocking buffer and fixed in 4% paraformaldehyde/4% sucrose (PFS) for 5 minutes, blocked with BSA for 10 min, rinsed and exposed to primary antibodies (3 at a time) at (1:100 to 1:500 dilution) for 1 hour at room temperature. Prior to use, primary antibodies were conjugated with Alexa Fluors 488 (ex/em, 495/519), 568 (ex/em 578/603) and 647 (ex/em 650/668) using the Zenon IgG labeling kits (Molecular Probes). Following incubation, the plates were rinsed 3 times with PBS. Multi-well plates were read on a Cytofluor 2350 fluorescence plate reader using the appropriate filters. Because the Cytofluor 2300 does not have multiplexed reading capabilities, the plate was scanned for each antibody. To ascertain that photo-bleaching of the dyes during the scanning did not affect the result, plates were scan in a different order for each experiment.

Western Blotting.

Following drug treatment, protein complexes were denatured in 50 μl of 2× loading buffer (200 mM Tris-HCl, pH 6.8, 4% SDS, 20% glycerol, 0.02% bromophenol blue, and 4% β-mercaptoethanol). All samples were transferred in microcentrifuge tubes, boiled for 5 min, centrifuged for 1 min, and 40 μl of each sample was loaded in a 7.5% SDS polyacrylamide gel. The loaded gel is electrophoresed and transferred to a nitrocellulose membrane from Bio-Rad, Hercules, Calif., USA. The nitrocellulose membrane was blocked with 5% milk, washed and incubated overnight with 1:1000 dilution of one of the following antibodies: anti-pTyr (4G10), anti-NR2A/B, anti-NR1, anti-PSD-95. After washing, the membranes were then incubated with the appropriate horseradish peroxidase-conjugated secondary antibodies and developed by chemiluminescence reagent from NEN Renaissance™ (NEN Life Sciences) using a Kodak Digital Science 4400CF Imager. Between incubations with antibodies that recognize the same bands, the membranes were stripped once in 62.5 mM Tris (pH 6.8), 2% SDS and 0.7% β-mercaptoethanol.

Buffer Compositions:
Novel Solubilization/Immunoprecipitation Buffer Composition:
0.1% Triton X-100
0.2% β-mercaptoethanol,
50 mM Tris-HCl pH 7.5,
5 mM EDTA,
5 mM EGTA
10 mg/ml of protease inhibitor cocktail
1 mM phenylmethylsulfonyl fluoride (protease inhibitor)
Reaction Buffer Composition:
0.2% β-mercaptoethanol,
25 mM Tris-HCl pH 7.5,
30 mM $MgCl_2$,
20 mM $MnCl_2$,
0.5 mM DTT.
Blocking Buffer Composition:
0.05% DOC
0.1% SDS
1% Nonidet P-40
50 mM Tris-HCl pH 8
150 mM NaCl
5 mM EDTA,
5 mM EGTA
10 mg/ml of protease inhibitors cocktail
1 mM phenylmethylsulfonyl fluoride (protease inhibitor)
5 mM $Na_3VO_4$
50 mM NaF
10 mM $NaPP_1$
25 mM Na-glycerophosphate
2 µM Microcystin-LR The N-methyl-D-aspartate receptor (NMDAR) complex is involved in several neurodegenerative diseases. Indeed, inappropriate activation of NMDAR, a subtype of glutamate receptors, results in excessive calcium influx and can cause excitotoxic neuronal death. Thus, blockage of NMDARs is neuroprotective in animal models (Lee et al., 1999) and suitable to treat NMDA related disorders in the central nervous system. These disorders include but are not limited to ischemia, pain, Alzheimer, Parkinson, schizophrenia, epilepsy, depression, migraine, inflammation and other neurodegenerative diseases. Because of the disappointment of NMDAR antagonists as neuroprotectors in clinical trials (ref), there is a real need for novel therapeutic drugs in this area. Pharmacological manipulation of the NMDAR complex with its associated protein and enzymes such as kinases and phosphatases, as distinct to NMDAR alone, may provide new therapeutic drugs that can modulate NMDAR without displaying the side effects of NMDAR antagonists. Preliminary results presented in this Example suggest that isolation of functional NMDAR complexes on 96-well plates, as an immunofluorescence-based HTS assay is feasible. Thus, creating a high throughput-screening tool for the discovery of neuroprotective drugs using NMDAR complexes as a target is a crucial tool for the pharmaceutical industry.

Background on NMDAR:

NMDARs are heteromeric assemblies composed of multiple subunits; these include NR1 subunits, a family of four distinct NR2 subunits (A, B, C and D) and two NR3 subunits (1 and s) (Dingledine et al., 1999; Das et al., 1998). NMDARs have been reported to interact with over 70 proteins involved in signaling, which include the postsynaptic density protein (PSD-95) (Husi et al., 2000). The function of these receptors is regulated by a series of phosphorylation and dephosphorylation processes mediated by protein kinases and protein phosphatases, respectively (Wang and Salter, 1994; Smart, 1997). Within NR1, phosphorylation by protein kinase C (PKC) and cAMP-dependent protein kinase (PKA) occurs at serine residues 890 and 896 (Ser890 and Ser896), and serine 897 (Ser897) (Tingley et al., 1993). NR2 subunits are phosphorylated by CaM kinase II (Gardoni et al., 1998), PKA, PKC (Leonard and Hell, 1997; Tingley et al., 1993), and protein tyrosine kinase (PTK) (Lau and Huganir, 1995). Protein tyrosine phosphatase (PTP) activity has been shown to co-immunoprecipitate with NMDARs (Ali and Salter, 2001), indicating that endogenous PTPs are intrinsic to the NMDAR complex. Recently several of these proteins have been identified as targets for NMDAR modulation such as PTK Src and Fyn, PKC, PKA and receptor PTPα (Wenthold et al., 2003). In addition, we have reported that compounds, such as PTP inhibitors, which have been shown previously to down regulate NMDAR (Coussens et al., 2000), and to display neuroprotective properties (Kawano et al., 2001; Lu et al., 2002), induce NMDAR subunits disassembly (Ferrani-Kile and Leslie, 2005). Thus, changes in NMDAR phosphorylation and protein-protein interaction between the subunits and/or the scaffolding proteins regulates the function of this receptor.

Rat NMDAR Versus Human NMDAR:

The final protein complexes immobilized on a 96 well-plates in this example were derived from rat brain tissue. Thus, a comparison between human and rodent NMDAR biology and signaling properties is provided. NMDA receptor channels are abundant in the human brain (Huntley et al. 1994; Scherzer et al. 1998), and appear to participate in glutamatergic synaptic transmission (Urban et al. 1990; Isokawa & Levesque, 1991; Masukawa et al. 1991; Hwa & Avoli, 1992; Isokawa et al. 1997). The cloned human NR1 subunit differs from that found in the rat by only seven of its 938 amino acids (Karp et al. 1993). Accordingly, the common features of homomeric human NR1 channels expressed in *Xenopus* oocytes include $Ca^{2+}$ permeability, voltage-dependent block by $Mg^{2+}$, antagonism by $Zn^{2+}$ and other competitive and non-competitive antagonists (Karp et al. 1993; Planells-Cases et al. 1993). Biochemical studies of human NMDA channel properties have described similarities to rodent receptors in the modulation of channel activity by polyamines (Subramaniam et al. 1994), and channels comprising human NR1a/NR2A and NR1a/NR2B subunits permanently transfected into mouse fibroblasts have electrophysiological properties comparable to their rodent counterparts. Additionally, the conductance of NMDA channels in adult human central neurons is similar to that of many other animal species. The distribution of openings and closures, and the number of exponential components in the distributions compare remarkably well with those observed in rat neurons prepared in an identical manner, and recorded under similar conditions (Köhr et al. 1993; Lieberman & Mody, 1994). Furthermore, the single-channel properties of synaptic and extrasynaptic NMDA receptors appear to be comparable (Lester et al. 1990; Clark et al. 1997). Thus, rodent NMDAR biology and signaling properties appear to be very similar to that of human and an array derived from rat brain tissue will be very useful for drug discovery for use in humans. Alternatively, NMDAR may be isolated from *Homo sapiens* and used in the same manner.

NMDAR complexes were extracted from untreated brain tissue immobilized on a protein A/G pre-coated 96-well plate as described above. The effect of SOV was tested as follows: immobilized complexes were rinsed and solubilization/immunoprecipitation buffer was replaced with a reaction buffer. This reaction buffer was added in all the was. Control wells contained only the reaction buffer or reaction buffer and ATP alone. Five mM SOV was added to rest of the wells and incubated at 30° C. for 1 hour. For immunoblot analysis, the reaction was stopped with blocking buffer and samples were rinsed and subjected to Western blotting with anti-pTyr, anti-NR2A/B, anti-NR1 and anti-PSD95 antibodies. Changes in NMDAR phosphorylation and protein-protein interaction between the receptor subunits and/or between the receptor subunits and proteins present in the complex, were assessed using immunoblotting and immunofluorescence detection methods. For fluorescence analysis, following incubation with the inhibitor, the reaction was stopped with blocking buffer, samples in the wells were rinsed, fixed in paraformaldehyde, incubated with Alexa-conjugated primary antibodies (anti-pTyr, anti-NR1 and anti-NR2A/B) with different em/ex wavelengths and read in a Cytofluor 2300 multi-plate fluorescence reader.

Figure 3A:
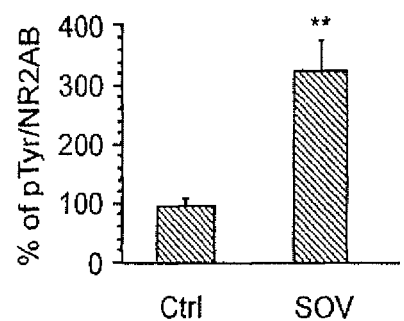
FIG. 3A-B. Immunofluorescence detection of the biological activity of immobilized NMDAR complexes: effect of PTP inhibitor SOV on immobilized complexes. Results are expressed as a ratio of pTyr to NR2A/B (A) and NR2A/B to NR1 (B). Each value is representative of four separate experiments. Data are mean S.E.M. Percent of control (**, $P<0.01$ control vs SOV).
Figure 3B:
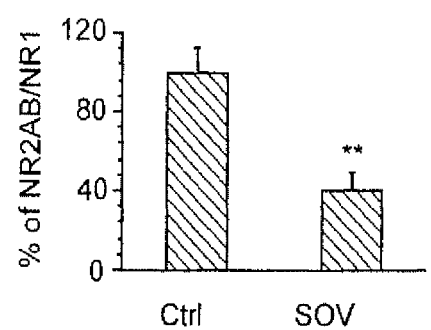

The results are presented in FIG. 2 (immunoblotting) and FIG. 3 (immunofluorescence). As can be seen, according to both methods of analysis, SOV increased tyrosine phosphorylation of NR2A/B subunits and decreased the amount of NR2A/B and PSD-95 in the receptor. These results are consistent with the experimental findings of Ferrani-Kile & Leslie (2005), who performed similar experiments using in situ cortical slices.

These results demonstrate that NMDAR complexes isolated and immobilized according to the methods of the invention are biologically active, and that their response to modulators (inhibitors and activators) is similar to that observed when NMDAR is tested in in situ brain slices, and can be detected by immunoblotting and fluorescence methods.

Example 2

Gamma-Amino Butyric Acid Receptor ($GABA_A$) Complexes

GABA is an inhibitory neurotransmitter in the CNS, and it binds to three distinct receptor subtypes: $GABA_A$, $GABA_B$, and $GABA_C$. $GABA_A$ receptors are responsible for most of the fast inhibitory synaptic transmission in the brain (Sivilotti and Nistri, 1991; Mody et al., 1994). $GABA_A$ receptors are thought to be heteropentameric structures and are formed of homologous subunits. Molecular cloning has thus far revealed a multiplicity of different $GABA_A$ receptor subunits divided into five different classes: α(1-6), β(1-4), γ(1-3), δ, and ρ(1-2) (Macdonald and Olsen, 1994; Smith and Olsen, 1995). The precise subunit composition and stoichiometry of native GABAA receptors are currently unknown, but the most abundant population of native $GABA_A$ receptors in the mammalian brain is believed to be the α1β2γ2 subunit combination (Benke et al., 1991; McKernan and Whiting, 1996). Each of the $GABA_A$ receptor subunits contains four transmembrane regions. The putative intracellular domain between the third and fourth membrane-spanning regions contains numerous potential consensus sites for protein phosphorylation by various protein kinases (Macdonald and Olsen, 1994; McKernan and Whiting, 1996). Previous investigations have shown that serine/threonine-specific phosphorylation modulates $GABA_A$ receptors (Browning et al., 1993; Raymond et al., 1993; Levitan, 1994). Moreover, modulation of $GABA_A$ receptors by tyrosine-specific phosphorylation in situ in CNS neurons has been studied by Qi Wan et al, (1997). This study provided evidence that endogenous PTKs are able to alter $GABA_A$ receptor activity via tyrosine phosphorylation of the β subunits. Given the prominent role of $GABA_A$ receptors in mediating many brain functions and dysfunctions, protein arrays containing $GABA_A$ receptor complexes are important for the study of a wide range of physiological and pathological processes.

To test the effect of PTP inhibitor SOV on isolated GABA receptor complexes, hippocampus tissue was removed and homogenized with the solubilization/immunoprecipitation buffer described above. $GABA_A$ receptor complexes were immunoprecipitated using anti-β2/β3 antibody (Upstate Biotechnology, Lake Placid, N.Y., USA) as described in Example 1. The immobilized complexes were rinsed and solubilization/immunoprecipitation buffer was replaced with reaction buffer. This reaction buffer was added to all the wells. Control wells contained only the reaction buffer or reaction buffer and ATP alone. Five mM of SOV was added to the rest of the wells and incubated at 30° C. for 1 hour. The reaction was stopped with a blocking buffer and samples rinsed and subjected to Western blotting with anti-pTyr and anti-β2/β3 antibodies.

Figure 4A:
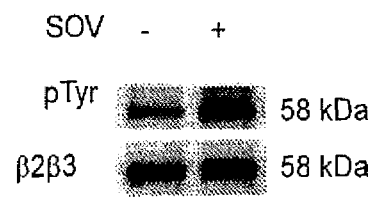
FIG. 4A-B. Stimulation of tyrosine phosphorylation in isolated $GABA_AR$ complexes: effect of PTP inhibitor SOV on isolated GABA receptor complexes. A, immunoblot; B, quantitation of immunoblot data. Results are expressed as a ratio of pTyr to β2/β3. Blots are representative of four separate experiments. Data are mean S.E.M. Net intensity (*, $P<0.05$ control vs SOV).
Figure 4B:
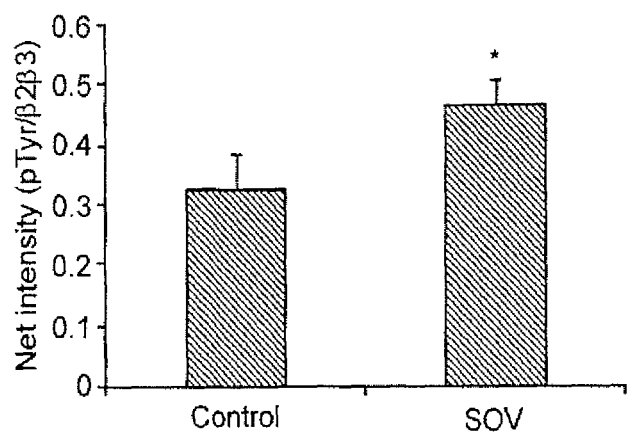

The results are presented in FIG. 4A-B. As can be seen, SOV increased tyrosine phosphorylation of β2/β3 subunits in the receptor. These results are consistent with the experimental findings of Qi Wan et al, (1997), who performed experiments showing that $GABA_A$ β2/β3 subunits can be phosphorylated at their tyrosine residues by endogenous PTK and exogenous PTK pp60c-src in cultured neurons.

These results demonstrate that $GABA_A$ receptor complexes isolated and immobilized according to the methods of the invention are biologically active, that their response to modulators (inhibitors and activators) is biologically relevant, and can be detected using standard laboratory methods.

Example 3

α-7 Nicotinic Acetylcholine Receptor Complexes

Nicotinic acetylcholine receptors are present in the central nervous system, the peripheral nervous system and neuromuscular junctions of somatic muscles. Similarly to $GABA_A$ receptors, glycine receptors, and the type 3 serotonin receptors, which are all classed within the nicotinicoid receptor family (Cascio, 2004), nicotinic receptors are formed by five receptor subunits, arranged symmetrically around the central pore. 17 nAChR subunits have been identified, and these are divided into muscle-type and neuronal-type subunits. Of these 17 subunits, α2-α7 and β2-β4 have been cloned in humans. In the muscle, the nAChR consist of two α subunits, a β, a δ and either a γ or an ε (Siegel et al., 1999) while in the nervous system nAChR are more heterogeneous, with a wide range of subunit combinations. α-7nAChRs are regulated by a variety of cellular mechanisms including phosphorylation. A direct role for cellular serine/threonine phosphorylation was demonstrated by the finding that calmodulin (CaM) kinase II inhibition could attenuate a use-dependent rundown of these receptors (Liu and Berg, 1999). Recently, it has become clear that tyrosine phosphorylation can very rapidly modulate receptor function (Davis et al., 2001 and Cho et al., 2005). In the following experiment, an assessment was made of whether the PTP inhibitor SOV has an effect on isolated and biologically active α-7nAChRs.

To test the effect of PTP inhibitor SOV on isolated a-7nACh receptor complexes, hippocampus tissue was dissected from the brain and homogenized with the solubilization/immunoprecipitation buffer described above, with some modifications. The solubilization buffer contained 0.05% TritonX-100 instead of 0.1% as used in Example 1. Immobilized complexes were rinsed and solubilization/immunoprecipitation buffer was replaced with reaction buffer. This reaction buffer was added to all the wells. Control wells contained only the reaction buffer or reaction buffer and ATP alone. Five mM SOV was added to rest of the wells and incubated at 30° C. for 1 hour. The reaction was stopped with a blocking buffer and samples rinsed and subjected to Western blotting with anti-pTyr, anti-α7 antibodies.

Figure 5A:
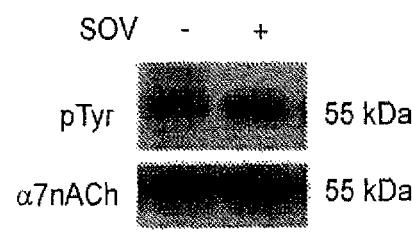
FIG. 5A-B. Stimulation of tyrosine phosphorylation in isolated α-7nAChR complexes: effect of PTP inhibitor SOV on immobilized complexes. A, immunoblot; B, quantitation of immunoblot data. Results are expressed as a ratio of pTyr to α-7. Blots are representative of four separate experiments. Data are mean S.E.M. Net intensity (*, $P<0.05$ control vs SOV).
Figure 5B:
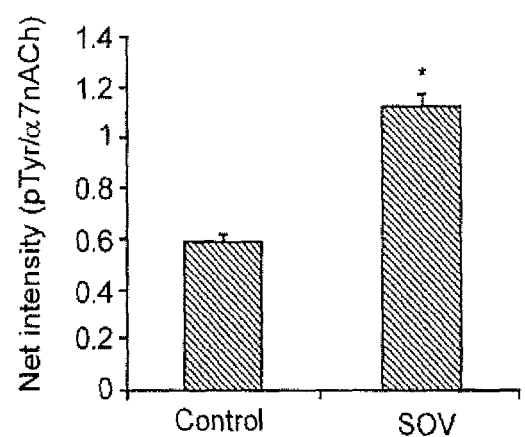

The results are presented in FIG. 5A-B. As can be seen, SOV increased tyrosine phosphorylation of β2/β3 subunits in the receptor. These results are consistent with the experimental findings of Charpentier et al., (2005), who performed experiments showing that tyrosine phosphorylation of regulation of α-7nACh receptor is modulated by genistein and pervanadate in SH-SY5Y neuroblastoma cells.

These results demonstrate that nAChR receptor complexes isolated and immobilized according to the methods of the invention are biologically active, that their response to modulators (inhibitors and activators) is biologically relevant, and can be detected using standard laboratory methods.

Example 4

Cyclic Nucleotide-Gated Ion Channel—HCN4

Cyclic nucleotide-gated ion channels are ligand-gated and are more similar in structure to the family of voltage-gated ion channels than to the ligand gated family. Cyclic nucleotide-gated channels are particularly important in the mammalian olfactory and visual systems but are also found in the heart. In the visual system, a cGMP (cyclic guanosine monophosphate) gated channel is found in the outer membrane of retinal photoreceptor cells. In response to high levels of cGMP, the channels are open and allow positively charged ions to flow into the cell, causing depolarization. Recently, Arinsburgn et al. (2005) reported that cardiac pacemaker current, if generated by hyperpolarization-activated cyclic nucleotide-gated (HCN) channels, is regulated by Src tyrosine kinase via phosphorylation of HCN4 in HEK293 cells and in rat ventricular myocytes.

To test the effect of PTP inhibitor SOV, rat ventricles were dissected and homogenized in solubilization/immunoprecipitation buffer and subjected to co-immunoprecipitation by incubation with anti-HCN4 polyclonal antibody (Alpha Diagnostic International, San Antonio, Tex.), as described in Example 1. Immobilized complexes were rinsed and solubilization/immunoprecipitation buffer was replaced with reaction buffer. This reaction buffer was added to all the wells. Control wells contained only the reaction buffer or reaction buffer and ATP alone. Five mM SOV was added to rest of the wells and incubated at 30° C. for 1 hour. The reaction was stopped with blocking buffer and samples were rinsed and subjected to Western blotting or fluorescence analysis using anti-pTyr and anti-HCN4 antibodies.

Figure 6A:
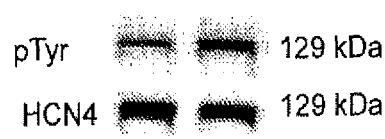
FIG. 6A-B. Stimulation of tyrosine phosphorylation in isolated HCN4R complexes: effect of PTP inhibitor SOV. A, immunoblot; B, quantitation of immunoblot data. Results are expressed as a ratio of pTyr to HCN4. Blots are representative of four separate experiments. Data are mean S.E.M. % of control (*, $P<0.05$ control vs SOV).
Figure 6B:
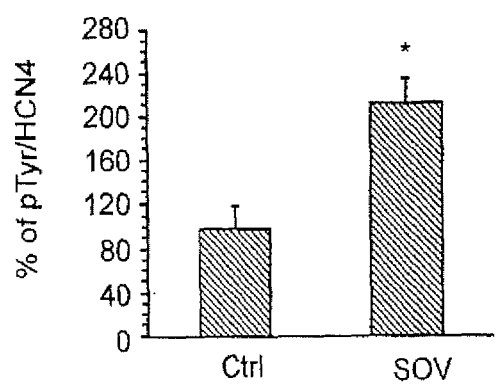

The results are presented in FIG. 6A-B. As can be seen, SOV increased tyrosine phosphorylation of HCN4 subunits in the receptor. These results are consistent with the experimental findings of Arinsburgn et al. (2005), who performed experiments using Src tyrosine kinase to induce tyrosine phosphorylation of HCN4 in HEK293 cells and in rat ventricular myocytes.

These results demonstrate that HCN4 ion channel complexes isolated and immobilized according to the methods of the invention are biologically active, that their response to modulators (inhibitors and activators) is biologically relevant, and can be detected using standard laboratory methods.

Summary

These studies demonstrate the feasibility of developing protein arrays for use in HTS assays by preparing multiprotein complexes according to the invention. Biologically active multiprotein complexes can be isolated, and changes in phosphorylation and subunit interactions of the isolated complexes can be readily detected. This strongly suggests that endogenous scaffolding proteins such as kinases and phosphatases, which are necessary for such modulation to occur, remain associated with the multiprotein complex throughout isolation and immobilization. Finally, changes in phosphorylation of the biologically active, immobilized multiprotein complexes can be detected with fluorescence, a format widely used in the HTS industry.

Example 5

Isolation and Immobilization of Dopamine Receptors

Dopamine receptors are a class of metabotropic G protein-coupled receptors with the neurotransmitter dopamine as their endogenous ligand. There are five types of dopamine receptor, D1-D5. The D1 and D5 receptors are members of the D1-like family of dopamine receptors whereas the D2, D3 and D4 receptors are members of the D2-like family. These receptors are also regulated by phosphorylation and protein-protein interaction.

Dopamine receptor multiprotein complexes are extracted, immobilized and analyzed using the method that is described in Example 1.

Example 6

Isolation and Immobilization of Histamine Receptors

There are four known histamine receptors, H1, H2, H3, and H4 with several splice variants of H3 present in various species. Though all of the receptors are 7-transmembrane g protein coupled receptors, H1 and H2 are quite different from H3 and H4 in their activities. H1 causes an increase in phosphoinositol hydrolysis, H2 stimulates gastric acid secretion, and H3 mediates feedback inhibition of histamine. These receptors are also regulated by phosphorylation and protein-protein interaction.

Histamine receptor multiprotein complexes are extracted, immobilized and analyzed using the method that is described in Example 1.

REFERENCES

Arinsburg, S., Cohen I., and Yu H G. Constitutively Active Src Tyrosine Kinase Changes Gating of HCN4 Channels Through Direct Binding to the Channel Proteins. *J Cardiovasc Pharmacol.* 2006 April; 47(4): 578-586.

Asian, K., Gryczynski, I., Malicka, J., Matveeva, E., Lakowicz, J. R., Geddes, C. D. Metal-enhanced fluorescence: an emerging tool in biotechnology. *Curr. Opin. Biotechnol.* 2005, 16 (1), 55.

Browning M D, Endo S, Smith G B, Dudek E M, Olsen R W (1993) Phosphorylation of the $GABA_A$ receptor by cAMP-dependent protein kinase and by protein kinase C: analysis of the substrate domain. *Neurochem Res* 18:95-100.

Benke D, Mertens S, Trzeciak A, Gillessen D, Mohler H (1991) $GABA_A$ receptors display association of γ2-subunit with α1- and β2/3-subunits. *J Biol Chem* 266:4478-4483.

Cho C., Song W., Leitzell K., Teo E., Meleth D A., Quick W M. and Lester R J. Rapid Upregulation of α7 Nicotinic Acetylcholine Receptors by Tyrosine Dephosphorylation. The *Journal of Neuroscience*, 2005, 25(14): 3712-3723.

Cascio, M. 2004. Structure and function of the glycine receptor and related nicotinicoid receptors. *Journal of Biological Chemistry*, 279(19), 19383-19386.

Davis M J, Wu X, Nurkiewicz T R, et al. Regulation of ion channels by protein tyrosine phosphorylation. *Am J Physiol Heart Circ Physiol* 2001; 281:H1835-H1862.

Ferrani-Kile K and Leslie S W. Modulation of tyrosine phosphatase activity alters subunit assembly in NMDA receptor complex. *JPET.* 314: 86-93, 2005.

Huntley, G. W., Vickers, J. C., Janssen, W., Brose, N., Heinemann, S. F. & Morrison, J. H. (1994). Distribution and synaptic localization of immunocytochemically identified NMDA receptor subunit proteins in sensory-motor and visual cortices of monkey and human. *Journal of Neuroscience* 14, 3603-3619.

Husi H, Ward M A, Choudhary J S, Blackstock W P and Grant S G. Proteomic analysis of NMDA receptor-adhesion protein signaling complexes. *Nat. Neurosci.* 2000, 3:661-669.

Hwa, G. G. & Avoli, M. (1992). Excitatory synaptic transmission mediated by NMDA and non-NMDA receptors in the superficial middle layers of the epileptogenic human neocortex maintained in vitro. *Neuroscience Letters* 143, 83-86.

Isokawa, M., Levesque, M., Fried, I. & Engel, J. Jr (1997). Glutamate currents in morphologically identified human dentate granule cells in temporal lobe epilepsy. *Journal of Neurophysiology* 77, 3355-3369.

Isokawa, M. & Levesque, M. F. (1991). Increased NMDA responses and dendritic degeneration in human epileptic hippocampal neurons in slices. *Neuroscience Letters* 132, 212-216.

Karp, S. J., Masu, M., Eki, T., Ozawa, K. & Nakanishi, S. (1993). Molecular cloning and chromosomal localization of the key subunit of the human N-methyl-D-aspartate receptor. *Journal of Biological Chemistry* 268, 3728-3733.

Kohr, G., de Koninck, Y. & Mody, I. (1993). Properties of NMDA receptor channels in neurons acutely isolated from epileptic (kindled) rats. *Journal of Neuroscience* 13, 3612-3627.

Lakowicz, J. R., 1999. *Principles of Fluorescence Spectroscopy.* Kluwer, New York.

Lee J M, Zipfel G J and Choi D W. The changing landscape of ischaemic brain injury mechanisms. *Nature* 1999, 399:A7-A14.

Lieberman, D. N. & Mody, I. (1994). Regulation of NMDA channel function by endogenous $Ca^+$ dependent phosphatase. *Nature* 369, 235-239.

Levitan I B (1994) Modulation of ion channels by protein phosphorylation and dephosphorylation. *Annu Rev Physiol* 56:193-212.

Liu Q S, Berg K D (1999) Actin filaments and the opposing actions of CaM kinase II and calcineurin in regulating α7-containing nicotinic receptors on chick ciliary ganglion neurons. *J Neurosci* 19:10280-10288. 261-279.

Macdonald R L, Olsen R W (1994) GABAA receptor channels. *Annu Rev Neurosci* 17:569-602.

McKernan R M, Whiting P J (1996) Which GABAA-receptor subtypes really occur in the brain? *Trends Neurosci* 19:139-143.

Mody I, De Koninck Y, Otis T S, Soltesz I (1994) Bridging the cleft at GABA synapses in the brain. *Trends Neurosci* 17:517-525.

Planells-Cases, R., Sun, W., Ferrer-Montiel, A. V. & Montal, M. (1993). Molecular cloning, functional expression, and pharmacological characterization of an N-methyl-D-aspartate receptor subunit from human brain. *Proceedings of the National Academy of Sciences of the USA* 90, 5057-5061.

Pawson T, Scott J D. Signaling through scaffold, anchoring, and adaptor proteins. *Science* 1997, 278(5346): 2075-2080.

Raymond L A, Blackstone C D, Huganir R L (1993) Phosphorylation of amino acid neurotransmitter receptors in synaptic plasticity. *Trends Neurosci* 16:147-153.

Scherzer, C. R., Landwehrmeyer, G. B., Kerner, J. A., Counihan, T. J., Kosinski, C. M., Standaert, D. G., Daggett, L. P., VeliÜcelebi, G., Penney, J. B. Jr & Young, A. B. (1998). Expression of N-methyl-D-aspartate receptor subunit mRNAs in the human brain: Hippocampus and cortex. *Journal of Comparative Neurology* 390, 75-90.

Siegel G. J., Agranoff B. W., Fisher S. K., Albers R. W., and Uhler M. D. 1999. Basic Neurochemistry: Molecular, Cellular and Medical Aspects, Sixth Edition. GABA Receptor *Physiology and Pharmacology.* Sivilotti L, Nistri A (1991) GABA receptor mechanisms in the central nervous system. Prog Neurobiol 36:35-92.

Smith G B, Olsen R W (1995) Functional domains of GABAA receptors. *Trend Pharmacol* 16:162-168.

Urban, L., Aitken, P. G., Friedman, A. & Somjen, G. G. (1990). An NMDA-mediated component of excitatory synaptic input to dentate granule cells in 'epileptic' human hippocampus studied in vitro. *Brain Research* 515, 319-322.

Wan Q., Man HY., Braunton J., Wang W., Salter M W., Becker L., Wang Y T. Modulation of GABAA Receptor Function by Tyrosine Phosphorylation of β Subunits. *The Journal of Neuroscience*, 1997, 17(13): 5062-5069.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. An in vitro method of detecting biological activity of a multiprotein complex to at least one substance, comprising the steps of:
    isolating by precipitation said multiprotein complex from a biological sample using a non-denaturing buffer which is 0.1% Triton X-100, 0.2% β-mercaptoethanol, 50 mM Tris-HCl, 5 mM EDTA, 5 mM EGTA, 10 mg/ml of protease inhibitor cocktail and 1 mM phenylmethylsulfonyl fluoride, and has a pH of 7.5, wherein said multiprotein complex retains biological activity in vitro, said multiprotein complex comprising i) at least one protein selected from the group consisting of α-7 nicotinic acetylcholine receptor, gamma-amino butyric acid receptor, and N-methyl d-aspartate receptor and ii) at least one scaffolding protein, wherein said multiprotein complex is immobilized on a substrate via an antibody that is attached to said substrate and is specific for said at least one, protein;

washing said multiprotein complex in a reaction buffer;

exposing in vitro said multiprotein complex to said at least one substance, wherein said step of exposing includes the steps of i) incubating said multiprotein complex and said at least one substance in said reaction buffer; and ii) terminating reactions of said multiprotein complex and said at least one substance using a blocking buffer; and detecting a presence or absence of a biological activity of said multiprotein complex to said at least one substance, wherein said biological activity is selected from a change in phosphorylation and a change in protein-protein interaction.

2. The method of claim 1 wherein said detecting step detects changes in at least one of the following: chemiluminescence, surface plasmon resonance, phosphorescence, fluorescence, and UV/Vis properties.

3. The method of claim 1, wherein said at least one scaffolding protein is selected from the group consisting of phosphatases, kinases, and post synaptic density components.

4. The method of claim 1, wherein said reaction buffer comprises 0.2% β-mercaptoethanol, 25 mM Tris-HCl pH 7.5, 30 mM $MgCl_2$, 20 mM $MnCl_2$, and 0.5 mM DTT.

5. The method of claim 1, wherein said blocking buffer comprises: 0.05% DOC, 0.1% SDS, 1% Nonidet P-40, 50 mM Tris-HCl pH 8, 150 mM NaCl, 5 mM EDTA, 5 mM EGTA, 10 mg/ml protease inhibitor cocktail, 1 mM phenylmethylsulfonyl fluoride, 5 mM $Na_3VO_4$, 50 mM NaF, 10 mM $NaPP_1$, 25 mM Na-glycerophosphate and 2 μM Microcystin-LR.

\* \* \* \* \*